(12) United States Patent
Lok et al.

(10) Patent No.: US 6,365,746 B1
(45) Date of Patent: *Apr. 2, 2002

(54) STABLE AND WATER SOLUBLE BIS AU(I) COMPLEXES AND THEIR SYNTHESIS

(75) Inventors: Roger Lok, Rochester; Weimar W. White, Canaseraga; Brian P. Cleary, Webster, all of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/473,249

(22) Filed: Dec. 27, 1999

Related U.S. Application Data

(62) Division of application No. 08/964,104, filed on Nov. 6, 1997, now Pat. No. 6,034,249.

(51) Int. Cl.[7] .................... C07D 233/84; C07D 249/12; C07D 257/04; C07D 307/64; C07D 333/64; C07F 1/12
(52) U.S. Cl. .......................... 548/106; 548/253; 549/3; 549/210; 556/113; 556/117
(58) Field of Search .................... 548/106; 556/113, 556/117; 549/3, 210

(56) References Cited

U.S. PATENT DOCUMENTS

| | | |
|---|---|---|
| 3,503,749 A | 3/1970 | Tavernier et al. ............. 96/107 |
| 4,840,871 A | 6/1989 | Peters et al. ................ 430/203 |
| 5,049,484 A | 9/1991 | Deaton ....................... 430/605 |
| 5,220,030 A | 6/1993 | Deaton ....................... 548/105 |
| 5,252,455 A | 10/1993 | Deaton ...................... 430/605 |
| 5,391,727 A | 2/1995 | Deaton .......................... 540/1 |
| 5,620,841 A | 4/1997 | Lok et al. ................... 430/600 |
| 5,700,631 A | 12/1997 | Lok et al. ..................... 43/600 |
| 5,945,270 A * | 8/1999 | Lok et al. ................... 430/605 |
| 6,034,249 A | 3/2000 | Lok et al. ................... 548/253 |

FOREIGN PATENT DOCUMENTS

DE    0578488    * 7/1931

OTHER PUBLICATIONS

Japanese Abstract No. 8069075 A, Derwent Info. Ltd.
Chemical Abstracts, vol. 118, No 15, Apr. 12, 1993, Columbus, Ohio, Abstract No. 139288.
Chemical Abstracts, vol. 107, No. 2, Jul. 13, 1987, Columbus, Ohio, Abstract No. 16633.

* cited by examiner

Primary Examiner—Floyd D. Higel
(74) Attorney, Agent, or Firm—Sarah Meeks Roberts

(57) ABSTRACT

This invention relates to an organomercapto Au(I) complex having the formula

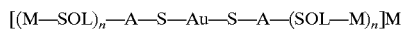

$[(M-SOL)_n-A-S-Au-S-A-(SOL-M)_n]M$ wherein M is a cationic counterion;

SOL is a solubilizing group:

A is a substituted or unsubstituted divalent organic linking group;

and n is 1 to 4 and wherein the compound is symmetrical. It further relates to a method of manufacturing an organomercapto Au(I) complex comprising reacting an Au (I) complex with an organomercapto ligand and isolating the resulting organomercapto Au(I) complex from the reaction mixture.

14 Claims, No Drawings

STABLE AND WATER SOLUBLE BIS AU(I) COMPLEXES AND THEIR SYNTHESIS

CROSS REFERENCE TO RELATED APPLICATIONS

This is a Divisional application of U.S. Ser. No. 08/964,104 filed Nov. 6, 1997, now U.S. Pat. No. 6,034,249. This application relates to U.S. Ser. No. 08/965,507 filed Nov. 6, 1997, now U.S. Pat. No. 5,945,270.

FIELD OF THE INVENTION

This invention relates to new Au(I) complexes comprising an organomercapto ligand, and to the manufacture of such complexes.

BACKGROUND OF THE INVENTION

There has been considerable effort devoted to improving the sensitivity of silver halide emulsions to actinic radiation, thereby increasing the sensitivity of the photographic elements in which they are contained. In this regard, photographic chemists have attempted to vary the components of, or the processes for making, silver halide emulsions. One particularly preferred means by which to improve sensitivity has been to chemically sensitize photographic emulsions with one or more compounds containing labile atoms of gold, sulfur, selenium or the like. Examples of chemically sensitized photographic silver halide emulsion layers are described in, for example, Research Disclosure, Item No. 308119, December 1989, Section III, and the references listed therein. (Research Disclosure is published by Kenneth Mason Publications Ltd, Dudley Annex, 12a North Street, Emsworth, Hampshire PO 10 7DQ, England.)

Many gold sensitizers have been described. For example, U.S. Pat. No. 3,503,749 describes the use of water soluble Au(I) thiolate salts comprising one Au atom ligated to one sulfur containing ligand; U.S. Pat. No. 5,220,030 teaches the use of Au(I) compounds with bis mesoionic heterocycles; U.S. Pat. No. 5,252,455 and U.S. Pat. No. 5,391,727 disclose the use of Au(I), macrocyclic cationic sensitizers; U.S. Pat. No. 5,049,484 teaches the use of Au(I) sensitizers having a Au atom ligated to the nitrogen atom of heterocyclic rings. U.S. Pat. No. 5,620,841 discloses the use of gelatin dispersions of a Au(I) thiosulfonato sensitizer with two different ligands at least one of which is mesoionic; and U.S. Ser. No. 08/672,254 teaches the use of gelatin dispersions of Au(I) thiosulfonato sensitizers with two different ligands at least one of which is a thioether group. JP 8069075 discusses the use of organic gold sulfide compounds in the sensitization to give low fogging and high contrast silver halide photographic materials. However, all of the above compounds have one or more disadvantages such as lack of water solubility, difficulty of synthesis or poor stability.

One common chemical sensitizer used in the sensitization of silver halide emulsions is aurous sulfide which is made as a colloidal gelatin dispersion, the exact composition of which is not well characterized. This gold sulfide dispersion can give rise to lot-to-lot variability and undesirable and inconsistent sensitometric performnance. The source of this variability may come from side reactions in the preparation of this highly insoluble solid since these reactions produce species which may be photographically active. Further, because of the highly insoluble nature of gold sulfide, most of the sensitizer added is in fact unused during the sensitization. The remaining sensitizer left in the gel/silver halide matrix can affect sensitometry.

The bis Au(I) mesoionic heterocycls e.g. bis(1,4,5-trimethyl-1,2,4-triazolium-3-thiolate) gold (I) tetrafluoroborate, TTT, while being a very useful sensitizer, is somewhat lacking in solution stability. Further, for the mesoionic triazolium sensitizers, multiple steps and recrystallizations are required in the preparation of the starting material bis(tetramethylthiourea) Au(I) tetrafluoroborate. Synthesis of the gold ligand 1,4,5-trimethyl-1,2,4-triazolium-3-thiolate is difficult, and the preparation of the mesoionic triazolium sensitizer is limited to small batches. Finally, the limited solubility of the mesoionic triazolium sensitizers requires the use of a large volume of water for dissolution.

Thus, there is still need for Au (I) compounds that are stable, water soluble and well characterized. Further, they must be easily manufactured from readily available starting materials.

SUMMARY OF THE INVENTION

This invention provides organomercapto Au(I) complexes having the formula

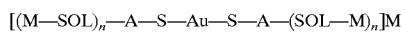

wherein

M is a cationic counterion;

SOL is a solubilizing group;

A is a substituted or unsubstituted divalent organic linking group;

and n is 1 to 4; and wherein the compound is symmetrical. This invention further provides a simple method of manufacturing an organomercapto Au(I) complex comprising reacting an Au(I) complex with an organomercapto ligand and isolating the resulting organomercapto Au(I) complex from the reaction mixture.

The novel organomercapto Au(I) complexes of this invention have numerous advantages. Unlike prior mixed-ligand gold compounds, the two Au ligands in this new class of compounds are identical, thus reducing the complexity of preparation. Further, the present invention employs inexpensive and commercially available materials for the generation of the necessary Au(I) species. Another advantage is that the preparation of the gold complexes of the present invention does not utilize dangerous explosive gold fulminates or large quantities of organic solvents.

Additionally, because of the stability of the covalent gold and sulfur bonds, the complexes of the present invention are more stable than those having mesoionic ligands. Indeed, there is evidence that even in acidic solutions, the complexes of the present invention are more stable than those of the mesoionic sensitizers.

The gold complexes of the present invention are also highly water soluble. Because of the water solubility of these complexes, the use of costly and time consuming preparation of gel dispersions is unnecessary. Further, there is no need to use large volumes of water for dissolving the complexes.

DETAILED DESCRIPTION OF THE INVENTION

The organomercapto Au(I) complexes of the invention are represented by the formula

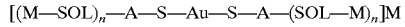

with the complex being symmetrical. M is a cationic counterion. Preferably M is an alkali metal, for example potassium, sodium or cesium, or an ammonium cation, for example, a tetrabutyl or tetraethyl ammonium group. SOL is a water solubilizing group, suitable examples of which are sulfato, sulfonato, sulfinato, phosphato, and carboxy groups. n is an integer from 1 to 4, and more preferably n is 1 or 2.

A is a substituted or unsubstituted divalent organic radical. Preferably A is an aliphatic, (cyclic or acyclic), aromatic or heterocyclic divalent group. When A is an aliphatic group, preferably it is a substituted or unsubstituted alphatic group having 1 to 20 carbon atoms, and more preferably having 1 to 8 carbon atoms. Examples of appropriate groups include alkylene groups such as ethylene, methylene, propylene, butylene, pentylene, hexylene, octylene, 2-ethylhexylene, decylene, dodecylene, hexadecylene, octadecylene, cyclohexylene, isopropylene and t-butylene groups.

The preferred aromatic groups have from 6 to 20 carbon atoms. More preferably, the aromatic groups have 6 to 10 carbon atoms and include, among others, phenylene and naphthylene groups. These groups may have substituent groups. The heterocyclic groups are preferably substituted or unsubstituted divalent 3 to 15-membered rings with at least one atom selected from nitrogen, oxygen, sulfur, selenium and tellurium in the ring nucleus. More preferably, the heterocyclic groups are 5 to 6-membered rings with at least one atom, and preferably more than one atom, selected from nitrogen. Examples of heterocyclic groups include the divalent radicals of pyrrolidine, piperidine, pyridine, tetrahydrofuran, thiophene, oxazole, thiazole, imidazole, benzothiazole, benzoxazole, benzimidazole, selenazole, benzoselenazole, tellurazole, triazole, benzotriazole, tetrazole, oxadiazole, or thiadiazole rings. The preferred heterocyclic group is tetrazole.

Unless otherwise specifically stated, substituent groups which may be substituted on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be bonded to the remainder of the molecule by an atom of carbon, silicon, oxygen, nitrogen, phosphorous, or sulfur. Suitable substituents for A include, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy)butyramido, alpha-(3-pentadecylphenoxy)-hexanamiido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylaamino, p-dodecyl-phenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy. One particularly suitable substituent for A is a benzamido group.

Generally, the above groups and substituents thereof may include those having up to 48 carbon atoms, typically 1 to 36 carbon atoms and usually less than 24 carbon atoms, but greater numbers are possible depending on the particular substituents selected.

When A is substituted, (SOL—M), may be attached to the substituent. In one suitable embodiment A—(SOL—M)$_n$ (wherein n is 1) is

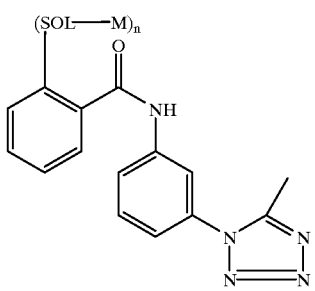

Specific examples of the Au(I) complexes include, but are not limited to
 (A)
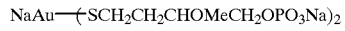 (B)
 (C)
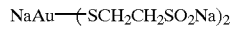 (D)
 (E)
 (F)
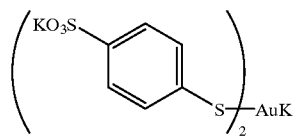 (G)
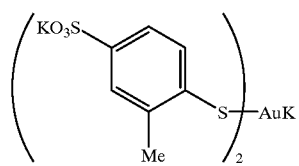 (H)
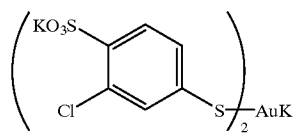 (I)
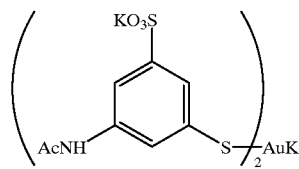 (J)
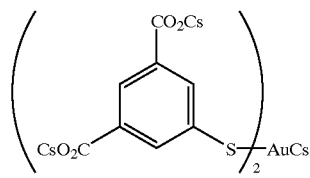 (K)
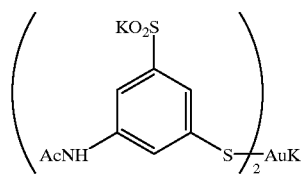 (L)
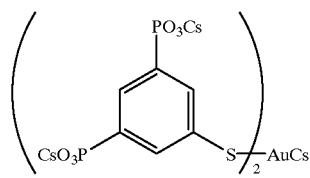 (M)
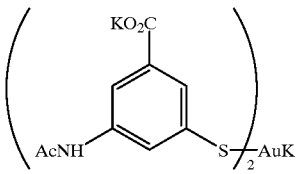 (N)
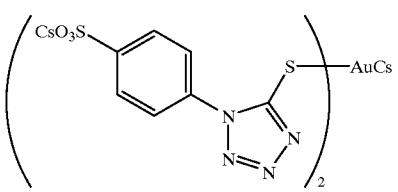 (O)
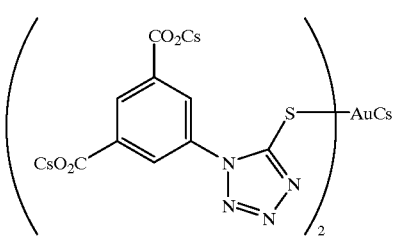 (P)
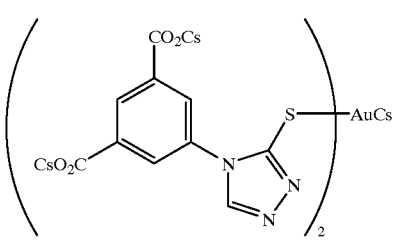 (Q)
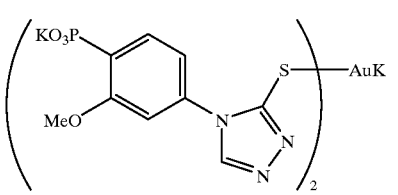 (R)
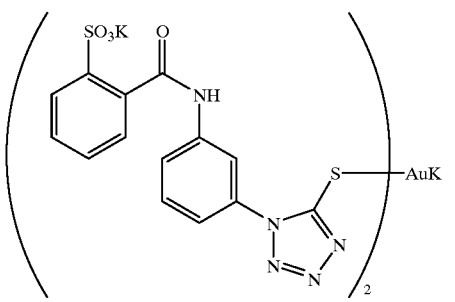 (S)
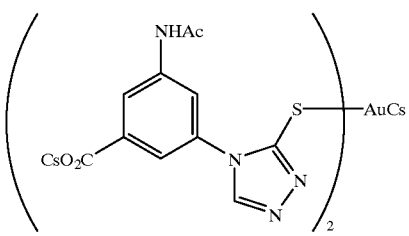 (T)

-continued

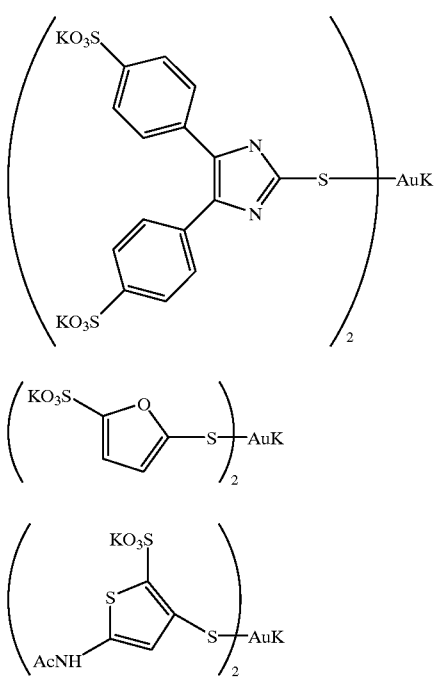

(U)

(V)

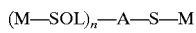

(X)

One particularly suitable complex is Compound S, potassium bis(1-[3-(2-sulfonatobenzamido)phenyl]-5-mercaptotetrazole potassium salt) aurate(I) pentahydrate.

One of the advantages of the complexes of this invention is their solubility in water. Preferably they have a solubility at 22° C. of 2 g/L, more preferably 5 g/L, and most preferably 10 g/L. Particularly suitable compounds have a solubility of greater than 20 g/L.

The organomercapto Au(I) complexes are manufactured by reacting an Au (I) complex with an organomercapto ligand and isolating the resulting organomercapto Au(I) complex from the reaction mixture. Suitable Au(I) complexes for use in this process are those having a more positive redox potential than the desired organomercapto Au(I) complex, thus allowing for the easy replacement of the ligand. Such compounds are known to those skilled in the art. Examples of some useful Au(I) complexes include $AuCl_2^-$, $AuBr_2^-$, $Au(MeS-CH_2-CH_2-CHNH_2COOH)_2^+$, $Au(C_3H_3N_2-CH_2-CH_2-NH_2)_2^+$, $Au(CNS)_2^-$, AuI, or $Au(NH_3)_2^+$, with AuI being particularly suitable.

Because the Au(I) complexes can be somewhat unstable, it is preferred to prepare them immediately before use by reacting a Au(III) compound with a stoichiometric amount of a reducing agent. The Au(III) compound can be any such compound which can be reduced to a stable Au(I) complex. Many of these compounds are commercially available. Examples of suitable compounds include $KAuBr_4$, $KAuCl_4$ and $HAuCl_4$. The reducing reagents may be, among others, tetrahydrothiophene, 2,2'-thiodiethanol, thiourea, N,N'-tetramethylthiourea, alkyl sulfides (eg. dimethylsulfide, diethylsulfide, diisopropylsulfide), thiomorpholin-3-one, sulfite, hydrogen sulfite, uridine, uracil, alkali hydrides and iodide. (Uson, R.; Laguna, A.; Laguna, M. *Inorg. Synth.* 1989, 26, 85–91; Al-Saady, A. K.; McAuliffe, C. A.; Parish, R. V.; Sandbank, J. A. *Inorg. Synth.* 1985, 23, 191–194; Ericson, A.; Elding, L. I.; Elmroth, S. K. C.; *J. Chem. Soc., Dalton Trans.* 1997, 7, 1159–1164; Elding, L. I.; Olsson, L. F. *Inorg. Chem.* 1982, 21, 779–784; Annibale, G.; Canovese, L.; Cattalini, L.; Natile, G. *J. Chem. Soc., Dalton Trans.*

1980, 7, 1017–1021). In some instances the reduction can be performed in the presence of a stabilizing agent such as potassium chloride (Miller, J. B.; Burmeister, J. L. *Synth. React. Inorg. Met.-Org. Chem.* 1985, 15, 223–233. In some instances it may be desirable to isolate the resulting Au (I) compound, i.e. to avoid undesirable side reactions. For example, in the case of AuI, removal of excess iodine is desirable to avoid deleterious sensitometric effects. Depending on the stability of the resulting Au(I) compound, however, its isolation may not be practical.

It is preferable that the Au(I) complex/organomercapto reaction be done in an aqueous system, however, as shown in the examples, this is not imperative. In general, the procedure requires no more than the mixing or stirring of the reagents for a short time, preferably at a temperature slightly above room temperature. The Au(I) compound is treated with at least two equivalents of a water soluble organomercapto ligand, preferably a water soluble salt of the ligand. Only one species of organomercapto ligand is utilized in the reaction in order to obtain a symmetrical mercapto Au(I) complex. Preferably the organomercaptide ligand has the formula (M—SOL)$_n$—A—S—M wherein M, SOL, A and n are as defined earlier for the organomercapto Au(I) complex. One suitable organomercaptide ligand is 1-[3-(2-sulfonatobenzamido)phenyl]-5-mercaptotetrazole potassium salt.

The reaction may be done in a very broad temperature range, preferably ambient to 100° C., and more preferably 30 to 50° C. Generally, the reaction can take place in the natural pH of the system, and does not need adjustment. It is believed that a fairly neutral pH, of about 4 to 7.5 is preferable, with a pH of about 6 being most preferable. In most cases the reaction of the Au(I) complex and the organomercapto ligand takes place in just a few minutes at a temperature of 30° C., although this may differ depending on the reactants. It may be necessary to add a stabilizing electrolyte such as Cl$^-$ or Br$^-$ when utilizing particularly unstable Au(I) complexes.

Isolation of the resulting Au(I) product may be achieved by any suitable method, for example by the treatment of the reaction mixture with several equivalents of an alkali halide or by the addition of a water miscible non-solvent. The solid Au(I) complex may be collected by filtration and dried in vacuo. The preferred method of isolation typically involves the introduction of an alkali halide followed by cooling of the reaction solution. The material is isolated by suction filtration and treated with chilled aqueous alcohol washes, such as butanol, isopropanol, ethanol etc. The procedure is straight forward with no complicated operations or multiple recrystallizations.

The organomercapto Au(I) complex may be used to sensitize a silver halide emulsion by the various techniques known to those skilled in the art. One suitable method includes adding the complexes to a silver halide emulsion as an aqueous solution and digesting the emulsion at a temperature in the range of 40 to 80° C.

The following examples are intended to illustrate, but not limit, the invention.

EXAMPLES

Example 1

Preparation of Compound S.5 H$_2$O. To a stirred, aqueous solution of KAuCl$_4$ (23.41 g in 172 mL water) was added 200 mL of a 4.22% (w/w) aqueous solution of NaI. The water was decanted from the dark brown solid and washed 3 times with 116 mL of water. Additionally, the solid was washed with several 116 mL aliquots of absolute ethanol until no color was observed in the ethanol phase. The remaining yellow solid was washed once with 116 mL of water and then quickly added to a stirred solution of 70 g of 1-[3-(2-sulfonatobenzamido)phenyl]-5-mercaptotetrazole potassium salt in 750 mnL of 30° C. water. The resulting solution was filtered and treated with 250 mL of 25% (w/w) aqueous KCl. Cooling to 5° C. yielded the product as a crystalline solid which was isolated by filtration, washed with 3×100 mL chilled (5° C.) isopropanol (60%), 2×100 nL chilled (5° C.) isopropanol (100%), dried in air by suction and then dried to 45° C. under $N_2$ to constant weight. The resulting material was equilibrated at 21° C. and 70% relative humidity to constant weight. Isolated yield was 65.3 g (91%). Compound S.5 $H_2O$ displays infrared, $^1H$ nuclear magnetic resonance and mass spectra that are consistent with materials possessing the molecular structures illustrated above. Elemental analyses were completed (theoretical values are shown parenthetically): C=29.2% (29.1%), H=2.2% (2.4%), N=12.1% (12.2%), S=11.1% (11.5%), Au=17.2% (17.1%).

Example 2

Preparation of Compound O. To a stirred, aqueous solution of $KAuCl_4$ (6.0 g in 50 mL water) was added 65 mL of a 4.22% (w/w) aqueous solution of NaI. The water was decanted from the dark brown solid and washed 3 times with 75 mL of water. Additionally, the solid was washed with several 75 mL aliquots of absolute ethanol until no color was observed in the ethanol phase. The remaining yellow solid was washed once with 75 mL of water and then quickly added to a warm (50° C.), stirred solution containing 21 g of 1-(4-sulfonatophenyl)-5-mercaptotetrazole potassium salt that has been dissolved in 200 mL of water and neutralized with aqueous $CsOH.H_2O$. An off white solid was obtained by filtration after the addition of 50 g of CsCl and cooling to 10° C. Crystallization from boiling water, and two successive washes of water and ethanol (2×150 mL, 0° C. and 2×150 mL, respectively) yielded the purified product. Compound O displays infrared, $^1H$ nuclear magnetic resonance and mass spectra that are consistent with materials possessing the molecular structures illustrated above. Elemental analyses were completed (theoretical values are shown parenthetically): C=15.8% (15.2%), H=1.2% (0.7%), N=10.6% (10.1%).

Example 3

Preparation of Compound P. To a stirred, aqueous solution of $KAuCl_4$ (7.0 g in 50 mL water) was added 70 mL of a 4.22% (w/w) aqueous solution of NaI. The water was decanted from the dark brown solid and washed 3 times with 35 mL of water. Additionally, the solid was washed with several 35 mL aliquots of absolute ethanol until no color was observed in the ethanol phase. The remaining yellow solid was washed once with 35 mL of water and then quickly added to a warm (50° C.), stirred solution containing 11.05 g of 1-(3, 5-dicarboxyphenyl)-5-mercaptotetrazole diacid that has been dissolved in 320 mL of water and neutralized with aqueous $CsOH.H_2O$. The addition of HCl led to the immediate precipitation of an off white solid. The solid was isolated, suspended in 200 mL of water and dissolved by the addition of an aqueous solution of $CsOH.H_2O$. Neutralization by the addition of HCl, followed by the addition of 2 L of absolute ethanol yielded the crude product. Purification was effected by recrystallization from an acetone and water solution. Compound P displays infrared, $^1H$ nuclear magnetic resonance and mass spectra that are consistent with materials possessing the molecular structures illustrated above. Elemental analyses were completed (theoretical values are shown parenthetically): C=16.3% (15.6%), H=1.2% (0.5%), N=8.2% (8.1%).

Example 4

Stability Study of Compound S. To a 1000 mL borosilicate volumetric flask was added 14.7 g of Compound S and water. An aliquot of the gold solution was placed into a quartz cuvette and the keeping characteristics of the solution were monitored using UV-visible spectroscopy over the course of 25 days. A compound, TTT, a known sensitizer having a mesoionic heterocycle was similarly monitored. The changes in absorbance was listed in the following Table. It can be seen that the compound of the present invention is more stable than TTT.

| | Change in Absorbance @ 235 nm | |
|---|---|---|
| Days | TTT | S |
| 1 | 0 | 0 |
| 4 | 0.0222 | 0.0013 |
| 8 | 0.0653 | 0.0015 |
| 13 | 0.0868 | 0.0058 |
| 20 | 0.1108 | 0.0070 |
| 25 | 0.1340 | 0.0064 |

Example 5

Stability of Compound S versus Compound TTT. Two different batches of Compound TTT and Compound S, each weighing 200 mg, were dissolved in 600 mL of a 0.025 N $H_2SO_4$. The solutions were allowed to stand at room temperature. One of the solutions containing Compound TTT had brownish colloidal gold precipitated within 5 days and the other batch had purplish gold specks after 7 days. There was no gold precipitate from the solution of Compound S after two weeks, the duration of the study.

Example 6

Solubility Study of compound S.5 $H_2O$. To a 10 mL borosilicate volumetric flask was added 0.25 g of Compound S and a stir bar. Water was added to the 10 mL mark and the suspension was stirred in the dark for 1 hr. The suspension was filtered through a 0.25 μm syringe filter and 3.00 mL of the filtrate was placed into a tared porcelain dish (dried by heating at 125° C. for 12 hours followed by cooling to ambient temperature in a $CaCl_2$ desiccator). The sample was placed into a vacuum desiccator and subjected to vacuum for ca. 60 hours. Finally, the dish and residue were weighed and the mass of the residue was determined by difference. Duplication yields an average solubility of 33.6 g/L.

Example 7

Although it is preferable to react the Au(I) complex with the mercaptide ligand in an aqueous system, it is possible to utilize organic solvents. One prophetic example is as follows. To an aqueous solution of a gold(III) salt is added an excess of a water miscible olefin. The mixture is stirred at a reduced temperature until a white precipitate is formed. The solid is isolated and dissolved in an appropriate organic solvent (methylene chloride, chloroform, toluene, benzene, acetone, tetrahydrofuran, etc.) to which is added 2 equivalents of the acid form of the mercaptan ligand. Tile mixture is stirred in the presence of a suitable Lewis base, $NR_3$ (triethyl amine, tripropyl amine, tributyl amine, etc.). The resulting ammonium salt is treated with M acetate or M hydroxide in the appropriate aqueous/organic solvent. The product is crystallized by the addition of a water miscible non-solvent.

In the example above, the gold (III) salt could be KAuCl4, HAuCl4, NaAuCl4 or MAuCl3(OH) where M=K, Na, etc. The water miscible olefin could be any olefin but literature precedence exists for cycloocta-1,5-diene, cis-2-butene, 5-decene, cyclooctene, cyclodecene, norbornene, norbornadiene and bicyclopentadiene. M acetate and M hydroxide where M is an alkali metal. A useful temperature range may be ca. −10 C. to −60 C.

The invention has been described in detail with particular reference to certain preferred embodiments thereof, but it will be understood that variations and modifications can be effected within the spirit and scope of the invention.

What is claimed is:

1. An organomercapto Au(I) complex having the formula

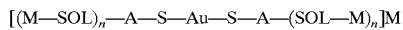

[(M—SOL)$_n$—A—S—Au—S—A—(SOL—M)$_n$]M wherein

M is an alkali metal or ammonium cation;

SOL is a sulfato, sulfonato, sulfinato, phosphate, or carboxy group;

A is a substituted or unsubstituted aliphatic group having 1 to 20 carbon atoms, an aromatic group have from 6 to 20 carbon atoms or a 3 to 15-membered heterocyclic ring with at least one atom selected from nitrogen, oxygen, sulfur, selenium or tellurium;

and n is 1 to 4; and wherein the compound is symmetrical.

2. The organomercapto Au(I) complex of claim 1 wherein A is a substituted or unsubstituted aliphatic group having 1 to 8 carbon atoms, an aromatic group having from 6 to 10 carbon atoms or a 5 to 6-membered heterocyclic ring with at least one atom selected from nitrogen.

3. The organomercapto Au(I) complex of claim 1 wherein A is a substituted or unsubstituted 5 to 6-membered heterocyclic ring with at least one atom selected from nitrogen.

4. The organomercapto Au(I) complex of claim 1 wherein M is sodium, cesium or potassium.

5. A method of manufacturing an organomercapto Au(I) complex comprising reacting an Au (I) complex with an organomercapto ligand of formula 1 and isolating the resulting organomercapto Au(I) complex from the reaction mixture

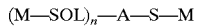

(M—SOL)$_n$—A—S—M wherein

M is an alkali metal or ammonium cation;

SOL is a sulfato, sulfonato, sulfinato, phosphato, or carboxy group;

A is a substituted or unsubstituted aliphatic group having 1 to 20 carbon atoms, an aromatic group have from 6 to 20 carbon atoms or a 3 to 15-membered heterocyclic ring with at least one atom selected from nitrogen, oxygen, sulfur, selenium or tellurium;

and n is 1 to 4.

6. The method of claim 5 wherein the Au (I) complex is prepared by reducing an Au (III) compound with a stoichiometric amount of a reducing agent.

7. The method of claim 5 wherein the reaction is done in an aqueous media.

8. The method of claim 5 wherein A is a substituted or unsubstituted aliphatic group having 1 to 8 carbon atoms, an aromatic group having from 6 to 10 carbon atoms or a 5 to 6-membered heterocyclic ring with at least one atom selected from nitrogen.

9. The method of claim 5 wherein A is a substituted or unsubstituted 5 to 6-membered heterocyclic ring with at least one atom selected from nitrogen.

10. The method of claim 5 wherein M is sodium, cesium or potassium.

11. The method of claim 7 wherein the Au(I) complex has a more positive redox potential than the redox potential of the desired organomercapto Au(I) complex.

12. The method of claim 7 wherein the Au(I) complex is $AuCl_2^-$, $AuBr_2^-$, $Au(MeS—CH_2—CH_2—CHNH_2 COOH)_2^+$, $Au(C_3H_3N_2—CH_2—CH_2—NH_2)_2^+$, $Au(CNS)_2^-$, AuI, or $Au(NH_3)_2^+$.

13. The method of claim 7 wherein the organomercapto Au(I) complex is isolated from the reaction mixture by the introduction of an alkali halide, followed in order by i) filtration and ii) treatment with one or more chilled aqueous alcohol washes.

14. The method of claim 13 wherein the filtration step is preceded by the cooling of the reaction mixture.

\* \* \* \* \*